(12) United States Patent
Mah

(10) Patent No.: US 11,786,349 B1
(45) Date of Patent: Oct. 17, 2023

(54) PROTECTIVE DEVICES FOR MANAGING AERODYNAMICS AROUND DENTAL PATIENTS

(71) Applicant: James Mah, Las Vegas, NV (US)

(72) Inventor: James Mah, Las Vegas, NV (US)

( * ) Notice: Subject to any disclaimer, the term of this patent is extended or adjusted under 35 U.S.C. 154(b) by 292 days.

(21) Appl. No.: 17/307,119

(22) Filed: May 4, 2021

Related U.S. Application Data

(60) Provisional application No. 63/025,215, filed on May 15, 2020.

(51) Int. Cl.
    *A61C 19/00*    (2006.01)
    *A61C 17/06*    (2006.01)
    *A61B 90/00*    (2016.01)
    *A61B 90/40*    (2016.01)

(52) U.S. Cl.
    CPC ............ *A61C 19/007* (2013.01); *A61C 17/06* (2019.05); *A61B 90/05* (2016.02); *A61B 2090/401* (2016.02)

(58) Field of Classification Search
CPC ... A61C 17/06–08; A61C 17/10; A61C 17/14; A61C 17/065; A61C 19/007; A61B 90/05; A61B 90/40; A61B 2090/401; A61B 2217/005; A61B 46/00–40; A61M 16/009; A61D 13/11; A41D 13/04–046; A41D 13/1236–129
USPC .................................................. 128/863, 847
See application file for complete search history.

(56) References Cited

U.S. PATENT DOCUMENTS

| | | | | |
|---|---|---|---|---|
| 3,625,207 A | * | 12/1971 | Agnew | A41D 13/11 128/206.28 |
| 4,122,848 A | * | 10/1978 | Carpel | A61B 46/00 128/849 |
| 5,112,322 A | * | 5/1992 | Hathaway | A61J 19/00 604/317 |
| 5,513,632 A | * | 5/1996 | Nepon | A61M 16/009 128/200.28 |
| 5,730,153 A | * | 3/1998 | Chang | A61B 46/00 128/857 |
| 6,135,770 A | * | 10/2000 | Bembenek | A61C 5/82 433/136 |
| 9,289,015 B2 | * | 3/2016 | Kassis | A41B 13/103 |
| 11,571,287 B1 | * | 2/2023 | Roholt | B08B 15/04 |
| 2021/0378802 A1 | * | 12/2021 | Jeanmenne | A61C 17/10 |

* cited by examiner

*Primary Examiner* — Jacqueline T Johanas
*Assistant Examiner* — Shannel Nicole Belk

(57) ABSTRACT

A particulate collecting device for dental patients is disclosed. The device includes a pair of vertical flanges, with a first flange configured to be positioned and worn on a right side of a patient's chest and a second flange configured to be positioned and worn on a left side of the patient's chest. The vertical flanges have an inner contour that aerodynamically funnels air flow away from the patient's face. The device includes a protective sheet located between the vertical flanges. The device includes a particulate matter reservoir that is fluidly coupled to the vertical flanges and configured to receive funneled air, and particulates contained therein, from the vertical flanges. The device also includes a negative air pressure generator, which is fluidly coupled to the particulate matter reservoir and produces negative air pressure in a direction from a top area of the vertical flanges towards the particulate matter reservoir.

19 Claims, 2 Drawing Sheets

US 11,786,349 B1

PROTECTIVE DEVICES FOR MANAGING AERODYNAMICS AROUND DENTAL PATIENTS

CROSS-REFERENCE TO RELATED APPLICATIONS

This application claims priority to U.S. provisional patent application Ser. No. 63/025,215, filed on May 15, 2020.

FIELD OF THE INVENTION

The field of the present invention relates to devices that may be used to manage and control air flow around and in proximity of dental and orthodontic patients, with such air control management being effective to reduce the risk of unwanted contamination of dental and orthodontic professionals by microorganisms (including bacteria and viruses) and other harmful organic and inorganic particulate matter.

BACKGROUND OF THE INVENTION

Many procedures in dentistry generate splatter, aerosols, and other airborne particulate matter, which may include various harmful microorganisms (including dangerous bacteria and viruses)—as well as other harmful organic and inorganic particulates. Such conditions have traditionally been managed using intraoral vacuum evacuation, rubber dental dams, protective barriers for patients to wear (such as a dental bibs), personal protective equipment for dentists/orthodontists and their assistants, and combinations of the foregoing.

For example, procedures that utilize a rotary hand piece or an ultrasonic device often generate a mist, with the origin of such mist being the working location in a patient's mouth. A local high-pressure area is generated at this origin—and air pressure gradients and turbulence cause the mist to flow and expand into areas of lower pressure. The mist often swirls and expands outward with trace aerosol particles traveling to places several feet away from the patient (thereby exposing not only the dental/orthodontic professional who may be performing a procedure, but also assistants and technicians in proximity of such procedure). A majority of the mist follows a common pattern, most of which falls onto the patient's chest. Lesser amounts can be found on a dental/orthodontic professional's chest, face, and arms. The mist contains mostly water, but often also contains blood products, bacteria, viruses, and contaminants arising from the dental materials being used (including mercury, silica, and transitional metals, such as aluminum and iron). All of such biological, organic, and inorganic particulate contaminants can seriously harm dental and orthodontic professionals, in a myriad of different ways.

Accordingly, there is a significant and continuing need to improve the operatory environment of dental and orthodontic procedures, in the interest of the overall health and safety of the professionals and clinicians who perform such procedures. In addition to existing high-volume suctions, barriers, and personal protective equipment, there is an ongoing need to control and safely handle the aerosol mist around dental and orthodontic patients.

As the following will demonstrate, the devices of the present invention address these (and other) needs in the marketplace.

SUMMARY OF THE INVENTION

According to certain aspects of the present invention, particulate collecting devices adapted to be worn by dental and orthodontic patients are provided. The devices generally include a pair of vertical flanges, with a first flange configured to be positioned and worn on a right side of a patient's chest and a second flange configured to be positioned and worn on a left side of the patient's chest. The vertical flanges have an inner contour that is configured to aerodynamically funnel air flow away from the patient's face. The devices further include a protective sheet located between the vertical flanges (in certain embodiments, the protective sheet is connected to and resides between the two vertical flanges). In addition, the devices include a particulate matter reservoir that is fluidly coupled to the vertical flanges and configured to receive funneled air, and particulates contained therein, from the vertical flanges. The device also includes a negative air pressure generator, which is fluidly coupled to the particulate matter reservoir and is adapted to produce negative air pressure in a direction from a top area of the vertical flanges towards the particulate matter reservoir (i.e., away from the patient's face and towards the particulate matter reservoir).

The above aspects of the present invention are described and exemplified further in the Detailed Description set forth below.

DETAILED DESCRIPTION OF THE INVENTION

The following will describe, in detail, several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used, and made without departing from the scope and spirit of the invention.

Figure 1:
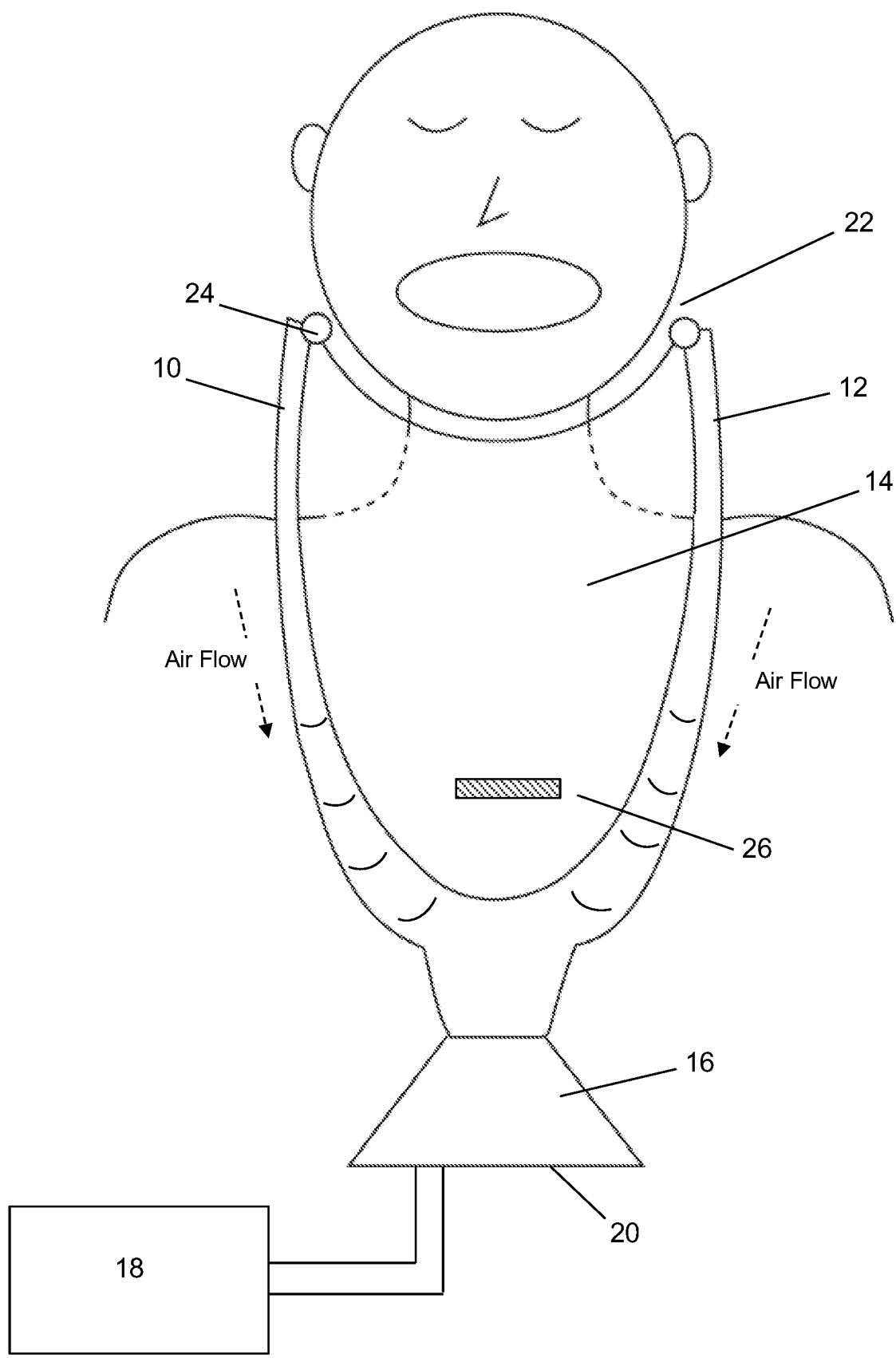
FIG. 1 is an illustration of the device described herein being worn by a dental/orthodontic patient.
Figure 2:
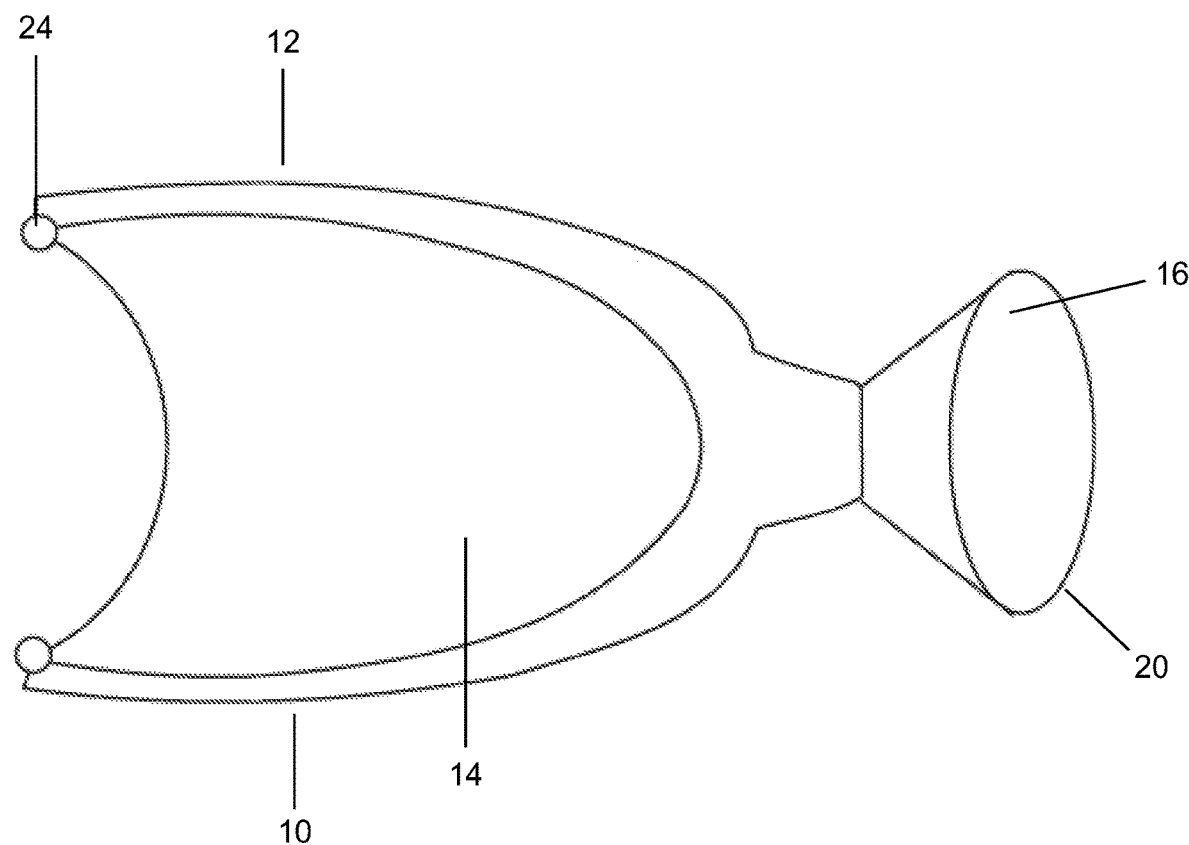
FIG. 2 is an illustration of the device described herein revealing a bottom area of the device.

Referring now to FIGS. 1 and 2, according to certain preferred embodiments of the present invention, particulate collecting devices adapted to be worn by dental and orthodontic patients (and to protect dental/orthodontic professionals in proximity thereof) are provided. The devices generally include a pair of vertical flanges 10/12, with a first flange 10 configured to be positioned and worn on a right side of a patient's chest and a second flange 12 configured to be positioned and worn on a left side of the patient's chest. The vertical flanges 10/12 have an inner contour that is curved and configured to aerodynamically funnel air flow away from the patient's face (and towards the particulate matter reservoir 16 described below). That is, the inner contour of the flanges 10/12 exhibit a curved and concave surface (relative to the patient's face), such that the flanges 10/12 are configured to aerodynamically funnel air flow away from the patient's face and towards the particulate matter reservoir 16.

The devices further include a protective sheet 14 located between the vertical flanges 10/12. The invention provides that, in certain embodiments, the protective sheet 14 will preferably connect the first flange 10 to the second flange 12. Still further, the invention provides that the protective sheet 14 may be affixed to the vertical flanges 10/12; whereas, in other embodiments, the protective sheet 14 may be integrally formed with the vertical flanges 10/12.

According to preferred embodiments of the present invention, the devices also include a particulate matter reservoir 16 that is fluidly coupled to the vertical flanges 10/12 and configured to receive funneled air, and harmful biological, organic, and inorganic particulates contained therein, from the vertical flanges 10/12. The device also includes a negative air pressure generator 18, which is fluidly coupled to the particulate matter reservoir 16 and is adapted to produce negative air pressure in a direction from a top area of the vertical flanges 10/12 towards the particulate matter reservoir 16. The invention provides that the negative air pressure generator 18 may generate a pneumatic suction force that produces the negative air pressure in a direction from a top area of the vertical flanges 10/12 towards the particulate matter reservoir 16.

According to certain preferred embodiments of the present invention, the particulate matter reservoir 16 preferably exhibits a funnel shape with a flat base 20, which is preferably configured to rest on the patient's chest. The invention provides that the upper half of the device is configured to rest on the patient's shoulders and chest, with the protective sheet 14 serving as a barrier between the mist, aerosol, and particulate matter described herein and the patient. The invention provides that the device will preferably include a hole, cut-out, or recessed area 22 that is adapted to surround the patient's head, with the hole, cut-out, or recessed area 22 exhibiting a dimension that matches, or substantially matches, contours of a patient's neck, lower jaw, and facial regions. In certain embodiments, the device may further include a mechanical means 24 for securing the device around the patient's head, such as a connecting arm (or other material that connects one side of the device, near the first flange 10, to the other side of the device, near the second flange 12).

In certain embodiments, the vertical flanges 10/12 may be adjusted to exhibit a desired length, e.g., to tailor the size and length of the device to the patient's head, shoulders, and chest. For example, the invention provides that the vertical flanges 10/12 may be adjusted to exhibit a desired length by trimming or folding each of the vertical flanges 10/12. In other embodiments, the invention provides that the device may be constructed in multiple sizes, which are designed to accommodate patients of different sizes within a typical range (e.g., sizes generally adapted for small, medium, and large pediatric patients and small, medium, and large adult patients). Still further, according to additional embodiments of the present invention, the device and the vertical flanges 10/12 thereof may be configured to extend upwards past the patient's ears (and to include and draw air flow away from the patient's forehead region).

Still further, the invention provides that the particulate collecting device may, optionally, include one or more perforations 26, which are configured to be attached to clips, strings, chains, dental appliances, or combinations of the foregoing. In addition, the one or more perforations 26 may further be configured to secure the particulate matter reservoir 16 to a desired location on the particulate collecting device.

In certain preferred embodiments of the present invention, the particulate collecting device will consist of, or consist essentially of, a disposable material. This way, following use with a patient, the soiled device may be discarded—and a new particulate collecting device can be used with a subsequent patient by the dental/orthodontic professional. Non-limiting examples of such disposable materials include paper, wood products, recyclable plastic, or combinations of the foregoing materials.

The many aspects and benefits of the invention are apparent from the detailed description, and thus, it is intended for the following claims to cover all such aspects and benefits of the invention, which fall within the scope and spirit of the invention. In addition, because numerous modifications and variations will be obvious and readily occur to those skilled in the art, the claims should not be construed to limit the invention to the exact construction and operation illustrated and described herein. Accordingly, all suitable modifications and equivalents should be understood to fall within the scope of the invention as claimed herein.

What is claimed is:

1. A particulate collecting device to be worn by a dental or orthodontic patient, which comprises:
   (a) a pair of vertical flanges, with a first flange configured to be positioned and worn on a right side of a patient's chest and a second flange configured to be positioned and worn on a left side of the patient's chest, wherein the vertical flanges have an inner contour that is curved and configured to aerodynamically funnel air flow away from the patient's face;
   (b) a protective sheet located between the vertical flanges;
   (c) a particulate matter reservoir that is fluidly coupled to the vertical flanges and configured to receive funneled air, and particulates contained therein, from the vertical flanges; and
   (d) a negative air pressure generator, which is fluidly coupled to the particulate matter reservoir and is adapted to produce negative air pressure in a direction from a top area of the vertical flanges and running downwards towards the particulate matter reservoir, wherein the particulate matter reservoir exhibits a funnel shape with a flat base that is configured to rest on the patient's chest.

2. The particulate collecting device of claim 1, which further comprises a hole or recessed area that is adapted to surround the patient's head, wherein the hole or recessed area exhibits a dimension that matches, or substantially matches, contours of a patient's neck, lower jaw, and facial regions.

3. The particulate collecting device of claim 1, wherein the device is configured to rest on the patient's shoulders.

4. The particulate collecting device of claim 1, which further comprises a mechanical means for securing the device around the patient's head.

5. The particulate collecting device of claim 1, wherein the vertical flanges may be adjusted to exhibit a desired length.

6. The particulate collecting device of claim 1, wherein the vertical flanges may be adjusted to exhibit a desired length by trimming or folding each of the vertical flanges.

7. The particulate collecting device of claim 1, which further comprises one or more perforations, which are configured to be attached to clips, strings, chains, dental appliances, or combinations of the foregoing.

8. The particulate collecting device of claim 7, wherein the one or more perforations are further configured to secure the particulate matter reservoir to a desired location on the particulate collecting device.

9. The particulate collecting device of claim 1, wherein the device consists of, or consists essentially of, a disposable material selected from the group consisting of paper, wood products, recyclable plastic, and combinations of the foregoing materials.

10. A particulate collecting device to be worn by a dental or orthodontic patient, which comprises:
 (a) a pair of vertical flanges, with a first flange configured to be positioned and worn on a right side of a patient's chest and a second flange configured to be positioned and worn on a left side of the patient's chest, wherein the vertical flanges have an inner contour that is curved and configured to aerodynamically funnel air flow away from the patient's face;
 (b) a protective sheet located between the vertical flanges;
 (c) a particulate matter reservoir that is fluidly coupled to the vertical flanges and configured to receive funneled air, and particulates contained therein, from the vertical flanges; and
 (d) a negative air pressure generator, which is fluidly coupled to the particulate matter reservoir and is adapted to produce negative air pressure in a direction from a top area of the vertical flanges and running downwards towards the particulate matter reservoir, wherein the particulate matter reservoir exhibits a funnel shape with a flat base that is configured to rest on the patient's chest.

11. The particulate collecting device of claim 10, which further comprises a hole or recessed area that is adapted to surround the patient's head, wherein the hole or recessed area exhibits a dimension that matches, or substantially matches, contours of a patient's neck, lower jaw, and facial regions.

12. The particulate collecting device of claim 11, wherein the device is configured to rest on the patient's shoulders.

13. The particulate collecting device of claim 12, which further comprises a mechanical means for securing the device around the patient's head.

14. The particulate collecting device of claim 13, wherein the vertical flanges may be adjusted to exhibit a desired length.

15. The particulate collecting device of claim 14, wherein the vertical flanges may be adjusted to exhibit a desired length by trimming or folding each of the vertical flanges.

16. The particulate collecting device of claim 15, which further comprises one or more perforations, which are configured to be attached to clips, strings, chains, dental appliances, or combinations of the foregoing.

17. The particulate collecting device of claim 16, wherein the one or more perforations are further configured to secure the particulate matter reservoir to a desired location on the particulate collecting device.

18. The particulate collecting device of claim 17, wherein the device consists of, or consists essentially of, a disposable material.

19. The particulate collecting device of claim 18, wherein the disposable material is paper, wood products, recyclable plastic, or combinations of the foregoing materials.

* * * * *